United States Patent [19]

Fülling et al.

[11] Patent Number: 5,426,211
[45] Date of Patent: Jun. 20, 1995

[54] VINYL 2-ARYL-PROPIONATES

[75] Inventors: Gerd Fülling, Frankfurt am Main; Merten Schlingmann, Königstein/Taunus; Reinhold Keller, Bad Soden, all of Germany

[73] Assignee: Hoechst Aktiengesellschaft, Frankfurt am Main, Germany

[21] Appl. No.: 903,755

[22] Filed: Jun. 25, 1992

Related U.S. Application Data

[62] Division of Ser. No. 535,149, Jun. 8, 1990, Pat. No. 5,155,028.

[30] Foreign Application Priority Data

Jun. 10, 1989 [DE] Germany ............... 39 19 029.3

[51] Int. Cl.$^6$ ............... C07C 69/62; C07C 69/614; C07C 69/616; C07C 69/618
[52] U.S. Cl. .................... 560/56; 560/105; 560/113
[58] Field of Search ............ 548/541; 549/79, 499; 560/56, 105

[56] References Cited

U.S. PATENT DOCUMENTS

| | | | |
|---|---|---|---|
| 3,960,893 | 6/1976 | O'Mant | 549/79 |
| 4,091,111 | 5/1978 | Ohno et al. | 549/79 |
| 4,107,178 | 8/1978 | Tsuchihashi et al. | 549/499 |
| 4,252,976 | 2/1981 | Guest et al. | 549/29 |
| 4,266,067 | 5/1981 | Fujisawa et al. | 549/29 |
| 4,309,439 | 1/1982 | Ohno et al. | 549/499 |
| 4,783,473 | 11/1988 | Hall et al. | 549/499 |
| 4,920,110 | 4/1990 | Neubauer et al. | 549/499 |

FOREIGN PATENT DOCUMENTS

| | | |
|---|---|---|
| 0153474 | 4/1985 | European Pat. Off. . |
| 0195717 | 9/1986 | European Pat. Off. . |
| 0227078 | 1/1987 | European Pat. Off. . |
| 0344656 | 8/1987 | European Pat. Off. . |
| 0299558 | 1/1989 | European Pat. Off. . |

OTHER PUBLICATIONS

M. Degueil-Castaing et al., Enzymatic Reactions in Organic Synthesis: 2-Ester Interchange of Vinyl Esters, Tet.Letters, v.28, N.9, pp. 953–954, 1987.

J. W. Young et al., Membrane Reactors For The Biocatalytic Production Of Chiral Compounds, Chiral 90 (1990) pp. 23–28.

Klaus Mosbach, Methods in Enzymology, vol. XLIV, Academic Press, (1976) pp. 263–267; 551–556.

Iriuchijima et al. "Asymmetric Hydrolysis of (±)—alpha-Substituted Carboxylic Acid Esters with Microorganisms" Agric. Biol. Chem., 45 (6), pp. 1389–1392 (1981).

*Primary Examiner*—David B. Springer
*Attorney, Agent, or Firm*—Finnegan, Henderson, Farabow, Garrett & Dunner

[57] ABSTRACT

In the enzymatic stereoselective ester cleavages of 2-arylpropionate, the reaction rate of the hydrolyzing enzymes can be drastically increased if the vinyl ester of the 2-arylpropionate is employed as the substrate.

6 Claims, No Drawings

VINYL 2-ARYL-PROPIONATES

This is a division of application Ser. No. 07/535,149, filed Jun. 8, 1990 now U.S. Pat. No. 5,155,028.

2-Arylpropionic acids have anti-inflammatory action. In the chemical synthesis of these compounds, the racemate is in general formed [J. P. Rieu et al. Tetrahedron Letters 42, 4095 (1986)]. However, it is known that in each case one of the enantiomers has a stronger biological action. In most cases this is the S-enantiomer [E. Hutt, J. Caldwell, Clin. Pharmac. 9 371 (1984)].

J. Iriuchijima et al. [Agric. Biol. Chem. 45 1389 (1981)] describe the microbial hydrolysis of naproxen and ketoprofen methyl esters which, however, stops at only a low conversion.

In EP 153,474, the cleavage of the racemate of lower alkyl 2-(6-methoxy-2-naphthyl)propionates is described. In this case, the R-acid is prepared in the first step of the process by incubation of the racemate with lipases from Aspergillus and Bacillus and in the second step the remaining S-ester is hydrolyzed using non-specific lipases from pig liver or *Pleurotus ostreatus*. High conversions can only be achieved by a continuous separation of the alcohol released during the cleavage, which would otherwise act on the enzyme in an inhibitory manner.

European Patent Application 195,717 relates to the preparation of S-2-arylpropionic acid by incubation of the racemic ester with a microbial esterase, in particular from *Candida cylindracea*. —$CH_2$=C≡CH, —$CH_2$—CH=$CH_2$, —$CH_2$—CN, —$CH_2$—$COCH_3$, —$CH_2$—COO—($C_1$-$C_4$) or —$CH_2$—O—($C_1$-$C_4$) are employed as ester groups. However, the conversion rate is relatively low. About 30 hours or more were required for a 40% conversion.

Even significantly lower conversion rates are described in EP 227,078. For the preparation of S-2-arylpropionic acid, the racemic alkyl esters are treated with microbial extracellular lipases for 6 days.

EP 233,656 likewise describes the hydrolysis of α-arylpropionates in the S-configuration with the aid of novel bacterial enzymes which have 10 times the activity of *Candida cylindracea*.

It has now surprisingly been found that the conversion rates of the enzymes in the hydrolysis of 2-arylpropionates, irrespective of whether they cleave the esters of the S- or R-configuration, are drastically increased if the vinyl ester of 2-arylpropionic acid is employed as a substrate.

The invention thus relates to a process for the enzymatic hydrolysis of 2-arylpropionates, which comprises incubating the compound of the general formula I

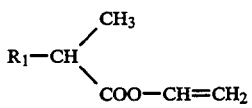

in which $R^1$ is a substituted or unsubstituted aryl radical, with hydrolases.

The invention, in particular in its preferred embodiment, is described in detail in the following. The invention is furthermore defined by the contents of the claims.

Compounds of the formula I are preferably employed in which the radical $R^1$ is the group of the formula II, III or IV

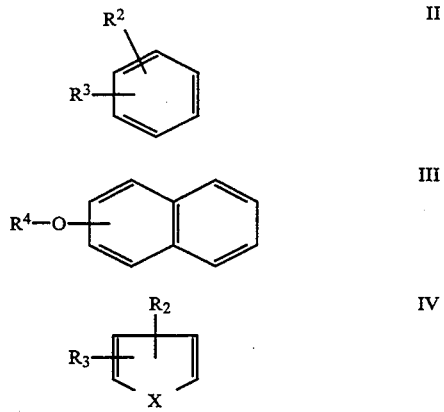

in which, independently of one another, $R^2$ is hydrogen, a branched or unbranched alkyl chain having 1 to 8 carbon atoms, alkenyl having 2 to 4 carbon atoms, alkoxy, benzoyl, phenyl, phenoxy, thiophenecarbonyl, furancarbonyl or pyrrolcarbonyl, $R^3$ is hydrogen or halogen, $R^4$ is an alkyl chain having 1 to 4 carbon atoms and X is the heteroatom S, O or N.

In the process according to the invention, the compound of the formula I is particularly preferably employed in which $R^1$ is the compound of the formula II or III, in which $R^2$ is hydrogen, a branched or unbranched alkyl chain having 1 to 8 carbon atoms, alkoxy or benzoyl, where $R^3$ and $R^4$ have the abovementioned meanings.

The racemic 2-arylpropionic acids are prepared by known processes (J. P. Rieu et al., see above). The preparation of the vinyl esters of these racemic 2-arylpropionic acids is carried out in a conventional manner, for example by esterification with vinyl acetate in the presence of palladium or mercury catalysts. (R. Hüttel, Synthesis 242 (1970)).

The vinyl esters of racemic 2-(6-methoxy-2-naphthyl)propionic acid (naproxen) and 2-(4-isobutylphenyl)propionic acid (ibuprofen) are particularly preferably employed.

Lipases, esterases or proteases, in particular those which are of microbial origin, can be used as hydrolases. Lipases or esterases from Pseudomonas, Mucor, Rhizopus, Penicillium, Geotrichum and, in particular, from Aspergillus, Candida and Bacillus, but also lipases and esterases from pig liver or pig pancreas are preferably used. Furthermore proteases from Bacillus, Aspergillus and Rhizopus are preferred, in particular from Aspergillus oryzae.

The enzymes are commercially available or can be isolated from the appropriate sources by conventional methods. The microbial enzymes can be isolated, for example, after cultivation of the microorganisms on conventional nutrient media by known methods. However, the whole microorganisms can also be employed for the reaction according to the invention.

The enzymes can be used in free or immobilized form, all common immobilization methods being suitable in this connection.

The amount of enzyme can vary within a wide range. It is selected depending on the size of the batch, on the reaction time desired and on the type of enzyme and can easily be determined by simple preliminary experiments in an individual case.

The substrate to be cleaved is employed, inter alia, in racemic form, i.e. as a 1:1 mixture of the S- and R-enantiomers. Often, however, the optical yield can be increased by employing already optically enriched substrate, obtained, for example, from the enzymatic hydrolysis, crystallization or the like, for the enzymatic cleavage.

The cleavage is carried out in suspension, it being possible to set a substrate/buffer ratio of 0.1% by weight to 30 % by weight; 1 to 10 % by weight is preferred.

The reaction is carried out at 10° to 65° C., preferably 20 to 50° C., the dependence of the activity of the particular enzyme on the temperature naturally having to be taken into consideration. The pH of the reaction solution is likewise, corresponding to the activity of the enzyme, in the range from pH 3 to 12, preferably 5 to 9, in particular between 6 and 8.5. The enzyme/substrate ratio can lie in the range from 0.05 % by weight to 100 % by weight, but preferably between 1 and 20 % by weight, depending on the reaction rate required. In the continuous column process, the local enzyme/substrate ratio which is due to the concentration of the substrate solution can even exceed 100 % by weight.

After the hydrolytic cleavage, the optical antipodes are present as the carboxylic acid or as the vinyl ester and can be separated according to their different physical or chemical behavior by distillation, crystallization, chromatography or other common processes, but preferably by extraction in such a way that the ester is exhaustively extracted at alkaline pH with a suitable organic solvent, such as, for example, chloroform, methylene chloride, tert.-butyl methyl ether, methyl isobutyl ketone etc., the acid initially remaining in the aqueous phase as the alkali metal salt. The 2-arylpropionic acid can then be precipitated as an amorphous precipitate at a low pH (pH 1 to 4) and centrifuged off or removed by extraction with the abovementioned solvents.

To increase the optical yield, the cleaved, optically enriched vinyl ester can be subjected to a repeated cleavage according to the process described above using the same or a different enzyme having the opposite stereoselectivity.

To release the free carboxylic acids from the optically active vinyl esters, an acid-catalyzed hydrolysis or, alternatively, a palladium salt-catalyzed transvinylation can be carried out in glacial acetic acid.

The preparation of optically active vinyl esters from the corresponding 2-arylpropionic acids succeeds, surprisingly with retention of the full optical activity, by means of palladium-catalyzed transvinylation in vinyl acetate. $Li_2PdCl_4$ on active carbon as the support material is preferably employed as a catalyst. The transvinylation is preferably carried out at the boiling point of the reaction mixture.

The vinyl 2-arylpropionates have a good anti-inflammatory action.

The invention is illustrated in more detail in the following examples. The percentage data relate to the weight, if not stated otherwise.

EXAMPLE 1

Preparation of the vinyl esters a) 100 g of 2-(4'-isobutylphenyl)propionic acid (ibuprofen) were taken up in 1 l of vinyl acetate and heated under reflux to boiling in the presence of 2 g of $Li_2PdCl_4$ and 20 g of active carbon. The reaction was followed by thin layer chromatography. After 8 hours, the catalyst was filtered off and the filtrate was concentrated to dryness. After filtration through silica gel using hexane:ethyl acetate (10:1), 92.7 g (39.9 mmol; 82%) of vinyl 2-(4'-isobutylphenyl)propionate were obtained as a clear oil.

b) 100 g (0.43 mol) of 2-(6-methoxy-2-naphthyl)propionic acid were converted into the vinyl ester analogously to Example 1a.

Yield: 87 g (78%) m.p.: 69° C.

EXAMPLE 2

Enzymatic ester cleavage 10 g (4.3 mmol) of vinyl 2-(4'-isobutylphenyl)propionate were suspended in 200 ml of 0.1M phosphate buffer (pH 7.0) and stirred after addition of 2 g of protease from Aspergillus oryzae (Sigma type XXIII).

The pH was kept constant by addition of 0.5M NaOH. After 24 hours, the reaction was stopped at a conversion of 53%. The remaining S-ester was then extracted at pH 8 with methylene chloride or methyl isobutyl ketone and the organic phase was concentrated to dryness.

a. Yield: 4.0 g (40%) of vinyl S-2-(4'-isobutylphenyl)-propionate $[\alpha]_D^{20} = +7$ (c=1, $CHCl_3$) ee ≧ 98% (enantiomer excess: determination by means of $^1$H-NMR after addition of shift reagent Eu (hfc)$_3$=tris[3-(heptafluoropropylhydroxymethylene)-(+)-camphorato]europium (III) derivative)

b. Yield: 3.1 g (35%) of R-2-(4'-isobutylphenyl)propionic acid $[\alpha]_D^{20} = -49$ (c=1, $CHCl_3$) ee: 85% (determination by means of $^1$H-NMR by conversion of the acid into the methyl ester with diazomethane and measurement of the methyl ester after addition of shift reagent Eu (hfc)$_3$)

EXAMPLES 3-7

200 (0.86 mmol) in each case of vinyl 2-(4'-isobutylphenyl)propionate were intensively stirred at room temperature with 50 mg in each case of enzyme in 5 ml of 0.5M phosphate buffer )pH 7.8). After completion of the reaction, the vinyl 2-(4'-isobutylphenyl)propionate remaining and 2-(4'-isobutylphenyl) propionic acid were separated as described under Example 2. The results are summarized in Tab. 1.

| Example | Enzyme | Reaction time [h] | Conversion [%] | Substrate ee [%][a] | Substrate Configuration | Product $[\alpha]_D^{20 b)}$ | Product ee [%][a] | Product Configuration |
|---|---|---|---|---|---|---|---|---|
| 3 | M-AP[c)d)] | 24 | 67 | 54 | S | −15 | 27 | R |
| 4 | F-AP[d)e)] | 5 | 38 | 18 | S | −16 | 29 | R |
| 5 | Type VII[f)h)] | 28 | 49 | 65 | S | −39 | 67 | R |
| 6 | Type XIX[f)g)] | 71 | 44 | 67 | S | −48 | 86 | R |

| Example | Enzyme | Reaction time [h] | Conversion [%] | Substrate ee [%][a] | Substrate Configuration | Product $[\alpha]_D^{20 b)}$ | Product ee [%][a] | Product Configuration |
|---|---|---|---|---|---|---|---|---|
| 7 | F 7[n) | 4 | 87 | 98 | R | +9 | 16 | S |

[a)]Determined as described under Example 2;
[b)]c = 1, CHCl$_3$;
[c)]Lipase from *Mucor javanicus*;
[d)]From Amano Pharmaceutical Co., LTD;
[e)]Lipase from *Rhizopus javanicus*;
[f)]From Sigma Chemie GmbH;
[g)]Protease from *Aspergillus sojae*;
[h)]Lipase from *Candida cylindracea*;
[n)]Lipases from Enzymatix LTD

EXAMPLES 8–20

200 mg (0.78 mmol) in each case of vinyl 2-(6-methoxy-2-naphthyl)propionate were intensively stirred at room temperature with 50 mg of enzyme in 5 ml of 0.5M phosphate buffer. After completion of the reaction, vinyl 2-(6-methoxy-2-naphthyl)propionate and 2-(6-methoxy-2-naphthyl)propionic acid were separated as described under Example 2. The results are summarized in Tab. 2.

pended in 50 ml of 0.1N phosphate buffer (pH 7.0) and, after adding 50 mg of lipase OF (from Candida cylindracea, Meito Sangyo LTD), stirred for 5 h at room temperature at constant pH (by metering in 0.1N NaOH). The mixture was then adjusted to pH 10 with NaOH, the unreacted vinyl ester was washed out with methylene chloride, the aqueous phase was then adjusted to pH 2 and the S-2-(4'-isobutylphenyl)propionic acid was extracted with methylene chloride. The organic phase was concentrated to dryness and the desired product was then recrystallized once from hexane.

| Example | Enzyme | pH | Reaction time [h] | Conversion [%] | Substrate ee [%][a] | Substrate Configuration | Product $[\alpha]_D^{20 b)}$ | Product ee [%][a] | Product Configuration |
|---|---|---|---|---|---|---|---|---|---|
| 8 | M-AP[c)d)] | 7.0 | 72 | 62 | 90 | S | n.d. | 55 | R |
| 9 | F-AP[d)e)] | 7.0 | 96 | 42 | 56 | S | −49 | 77 | R |
| 10 | Type XIX[f)g)] | 7.8 | 48 | 30 | 35 | S | n.d. | 80 | R |
| 11 | Type XXIII[f)o)] | 7.8 | 96 | 44 | 75 | S | n.d. | 95 | R |
| 12 | OF[i)k)] | 7.0 | 8 | 57 | 44 | R | n.d. | 30 | S |
| 13 | Protease N[d)l)] | 7.8 | n.d. | 13 | 10 | S | −46 | 70 | R |
| 14 | Subtilisin[m)] | 7.8 | n.d. | 53 | 52 | R | +30 | 46 | S |
| 15 | F1[n)] | 7.8 | 91 | 43 | 70 | S | −62 | 94 | R |
| 16 | F3[n)] | 7.8 | 24 | 45 | 74 | S | −59 | 90 | R |
| 17 | F5[n)] | 7.8 | 24 | 80 | 80 | R | +13 | 20 | S |
| 18 | F7[n)] | 7.8 | 24 | 68 | 78 | S | −19 | 37 | R |
| 19 | F8[n)] | 7.8 | 48 | 56 | 86 | S | −45 | 68 | R |
| 20 | PLE[f)] | 7.0 | 48 | 13 | 4 | S | −17 | 26 | R | n.d. = not determined
[a)–g), n)] see appropriate footnotes, Tab. 1
[h)]protease from *Aspergillus oryzae*
[i)]lipase from *Candida cylindracea*
[k)]Meito Sangyo Co LTD
[l)]protease from *Bacillus sp.*
[m)]Novo Industri
[o)]protease from *Aspergillus oryzae*

EXAMPLE 21

10 g (43 mmol) of racemic vinyl 2-(4'-isobutylphenyl)propionates were reacted for 7 h in 200 ml of 0.1M phosphate buffer (pH 7.0) in the presence of 200 mg of lipase OF (from *Candida cylindracea*, Meito Sangyo LTD) analogously to Example 2. The following were isolated:

a) 4.3 g (43%) of vinyl R-2-(4'-isobutylphenyl)propionate
$[\alpha]_D^{20} = -5$ (c=1, CHCl$_3$) ee=76% b) 4.2 g (47%) of S-2-(4'-isobutylphenyl)propionic acid
$[\alpha]_D^{20} = +37$ (c=1, CHCl$_3$) ee=68%

EXAMPLE 22

1 g (4.8 mmol) of S-2-(4'-isobutylphenyl)propionic acid (ee=68%) from Example 21 was reacted in 10 ml of vinyl acetate in the presence of 125 mg of Li$_2$PdCl$_4$ and 1.25 g of active carbon analogously to Example 1.

Yield: 900 mg (81%) of vinyl S-2-(4'-isobutylphenyl)propionate $[\alpha]_D^{20} = +5$ (c=1, CHCl$_3$) ee=68%

EXAMPLE 23

680 mg (2.9 mmol) of vinyl S-2-(4'-isobutylphenyl)propionate (ee=68%) from Example 22 were sus- Yield: 305 mg (51%) of S-2-(4'-isobutylphenyl)propionic acid $[\alpha]_D^{20} = +54$ (c=1, CHCl$_3$) ee=96%.

EXAMPLE 24

Cleavage of the S-ester 2.8 g (12.1 mmol) of S-ibuprofen vinyl ester from Example 2 are taken up in 60 ml of glacial acetic acid and stirred at 60°–70° C. in the presence of 200 mg of Li$_2$PdCl$_4$ on active carbon. After completion of the reaction (TLC checking), the catalyst is filtered off and the filtrate is concentrated to dryness. The mixture is taken up in methyl isobutyl ketone, is washed once with water and is concentrated to dryness. The residue is recrystallized once from hexane.

Yield: 2.4 g of ibuprofen (11.6 mmol) 96% $[\alpha]_D^{20} = +57$ (c=1, CHCl$_3$) ee:≧98%.

EXAMPLE 25

100 mg in each case of 2-(4'-isobutylphenyl)propionates ([a)]methyl, [b)]chloroethyl, [c)]vinyl) are suspended in 40 ml of 0.25M phosphate buffer (pH 7.8) and, after adding 100 mg of protease from Aspergillus oryzae (Sigma) at 35° C., titrated against 0.1N NaOH. The conversion is calculated by means of the NaOH metered in. FIG. 1 shows the time-conversion dependence of the enzymatic hydrolysis of the respective 2-(4'-isobutylphenyl)propionate.

We claim:

1. An optically active vinyl arylpropionate of the formula I

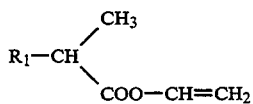
                      I in which $R^1$ is the group of the formula II

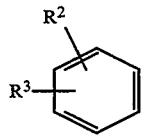
                      II in which, independently of one another, $R^2$ is hydrogen, a branched or unbranched alkyl chain having 1 to 8 carbon atoms.

$R^3$ is hydrogen or halogen.

2. An optically active vinyl arylpropionate of the formula I

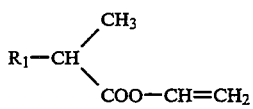
                      I in which $R^1$ is the group of the formula III

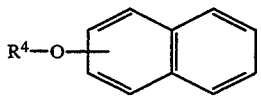
                      III $R^4$ is an alkyl chain having 1 to 4 carbon atoms.

3. The compound of claim 1, wherein said active vinyl arylpropionate is vinyl 2-(4'-isobutylphenyl)propionate.

4. The compound of claim 2, wherein said optically active vinyl arylpropionate is vinyl 2-(6-methoxy-2-naphthyl)propionate.

5. The compound of claim 1, wherein said optically active vinyl arylpropionate is vinyl R-2-(4'-isobutylphenyl)propionate.

6. The compound of claim 1, wherein said optically active vinyl arylpropionate is vinyl S-2-(4'-isobutylphenyl)-propionate.

* * * * *

UNITED STATES PATENT AND TRADEMARK OFFICE
CERTIFICATE OF CORRECTION

PATENT NO.  :  5,426,211
DATED       :  June 20, 1995
INVENTOR(S) :  Gerd FUELLING et al It is certified that error appears in the above-indentified patent and that said Letters Patent is hereby corrected as shown below:

CLAIM 1, COLUMN 7, LINE 29, delete "."
and insert --and--.

Signed and Sealed this

Eleventh Day of June, 1996

BRUCE LEHMAN

*Attest:*

*Attesting Officer*          *Commissioner of Patents and Trademarks*